US00PP11332P

United States Patent [19]

Eilers

[11] Patent Number: Plant 11,332

[45] Date of Patent: Apr. 4, 2000

[54] *BERBERIS THUNBERGII* PLANT NAMED 'MONRY'

[75] Inventor: Henry Eilers, Litchfield, Ill.

[73] Assignee: Monrovia Nursery Company, Azusa, Calif.

[21] Appl. No.: 09/031,100

[22] Filed: Feb. 26, 1998

[51] Int. Cl.[7] ..... A01H 5/00

[52] U.S. Cl. ..... Plt./241

[58] Field of Search ..... Plt./241

[56] References Cited

U.S. PATENT DOCUMENTS

| | | | |
|---|---|---|---|
| P.P. 8,215 | 4/1993 | Moretti | Plt./241 |
| P.P. 9,577 | 6/1996 | Eilers | Plt./241 |

OTHER PUBLICATIONS

Monrovia Wholesale Catalog 18331 E. Foothill Boulevard, Azusa, CA 91702, p. 50, 1999.

*Primary Examiner*—Howard J. Locker
*Assistant Examiner*—Wendy A Baker

[57] ABSTRACT

A new and distinct selection of Golden Barberry shrub which shall be referred to hereinafter as *Berberis thunbergii* 'Monry'. *Berberis thunbergii* 'Monry' differs distinctively from other *Berberis thunbergii* plants by its unique combination of early flower clusters and yellowish foliage produced along terminal branch tips and an upright vase-shaped shrub habit with brilliant yellow mature foliage that tolerates full sun without burning.

3 Drawing Sheets

BACKGROUND OF THE NEW PLANT

This invention relates to a new and distinct selection of *Berberis thunbergii,* a member of the Berberidaceae or Barberry family. *Berberis thunbergii* 'Monry' was discovered in a group of seedlings in 1977. The seedlings were a product of an uncontrolled cross but believed to be *Berberis thunbergii* 'Aurea' crossed with *Berberis thunbergii* 'Kobold'. This seedling was selected from 50 to 100 other seedlings as it exhibited relatively stout stiff branches and much smaller foliage than other selections. My new selection has been asexually reproduced by cuttings since the discovery at H E Nursery, R.R. 3, Box 4, Litchfield, Ill. 62056 and later at Monrovia Nursery Company, 13455 S. E. Lafayette Hwy., Dayton, Oreg. The original seedlings displayed extreme variability, therefore the distinct phenotypic characteristics of my new selection that sets this plant apart from other *Berberis thunbergii* plants would likely be lost through sexual reproduction. Therefore, sexual reproduction does not breed true to type and propagation is accomplished by asexual reproduction by cuttings.

SUMMARY OF INVENTION

*Berberis thunbergii* 'Monry' is unusual as it possesses an upright vase shape shrubby habit, whereas typical *Berberis thunbergii* cv. Aurea is a rounded shrub 1⅓ meters in height and with thin branches. My new selection after 10 years is 1 meter tall and 1 meter wide with smaller foliage and stouter branches when compared with cultivar Aurea. Cultivar Bogazam, U.S. Plant Pat. No. 8,215 is smaller in comparison 45 centimeters tall and 90 centimeters wide and has larger foliage. Cultivar Monlers U.S. Plant Pat. No. 9,577 is a smaller in comparison, 37 centimeters tall and wide and possesses larger foliage.

BOTANICAL DESCRIPTION

Figure 1:
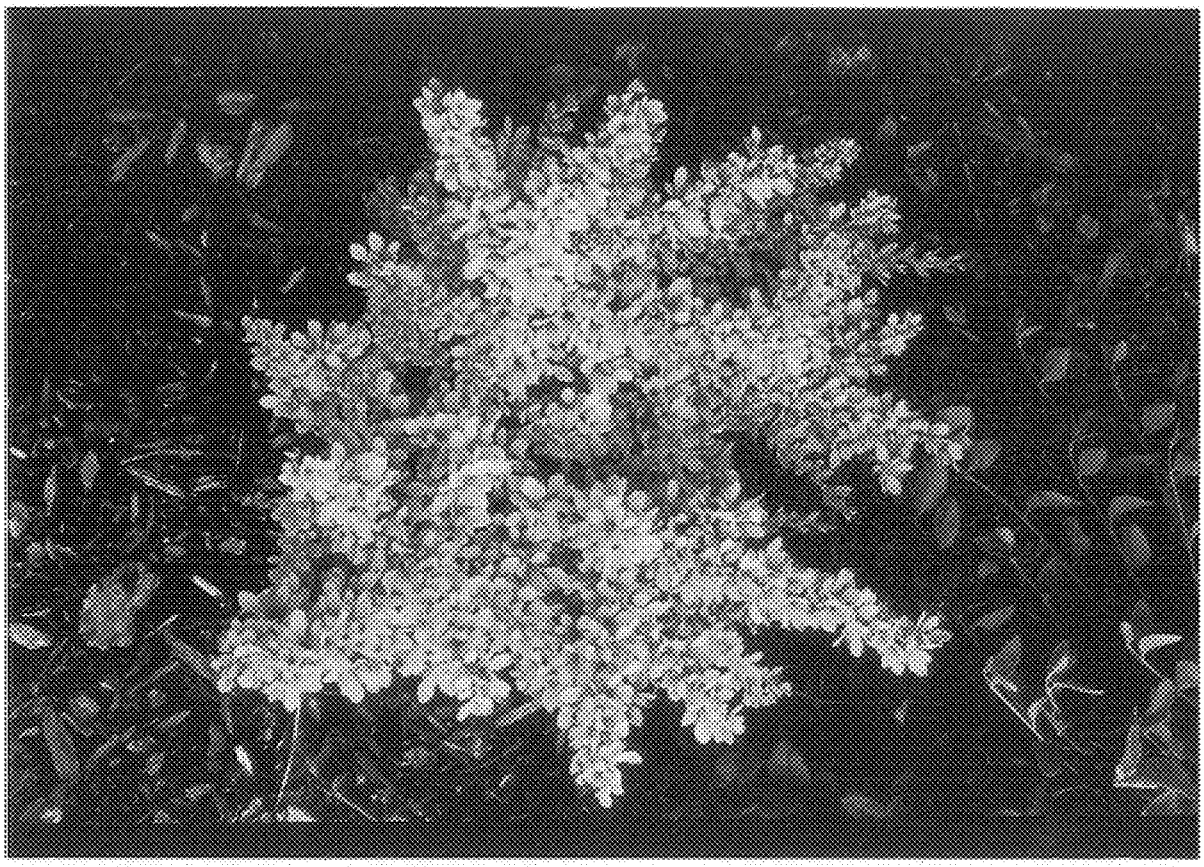
FIG. 1 shows 'Monry', depicting the golden spring foliage and the open upright vase-shaped habit. Cultivars 'Monler' and 'Bogazam' both have a tight dense growth habit.
Figure 2:
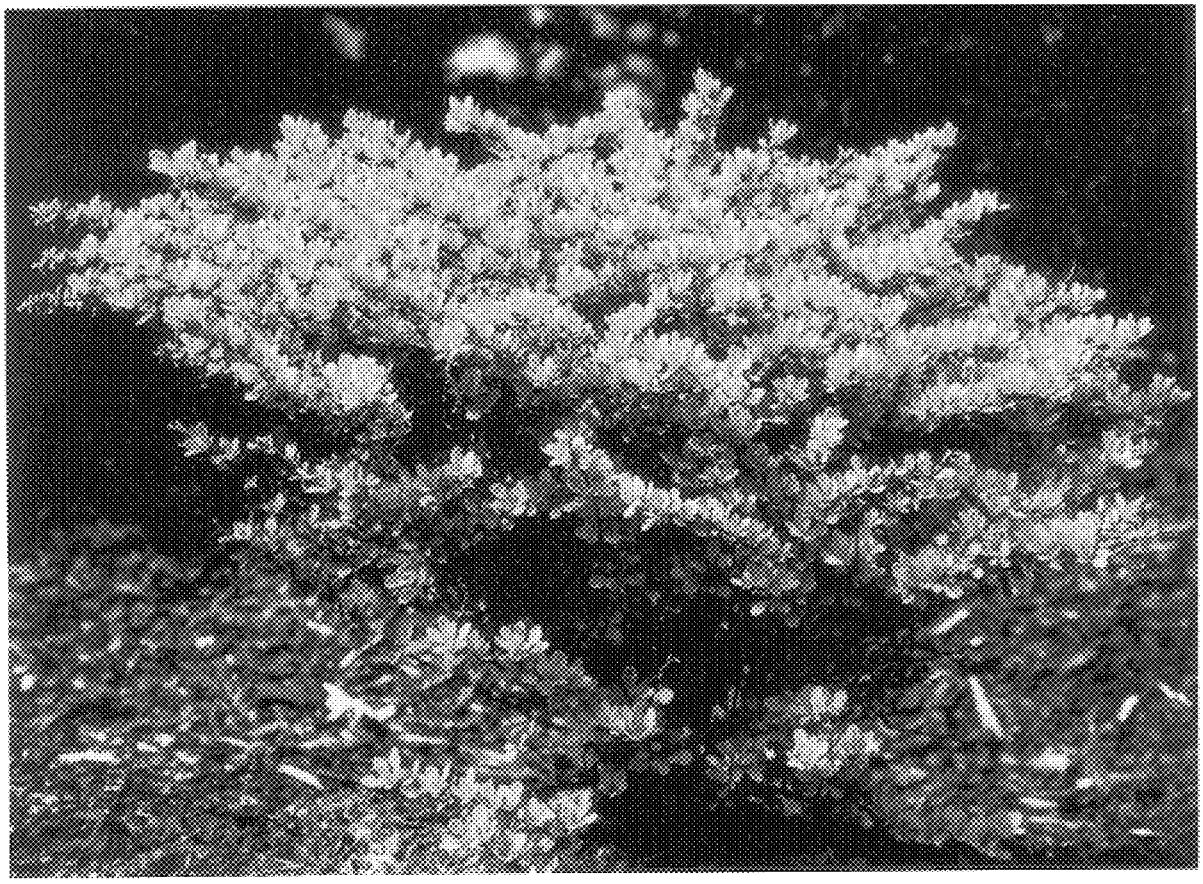
FIG. 2 illustrates a side view of the upright vase-shaped habit and the brilliant yellow mature foliage.
Figure 3:
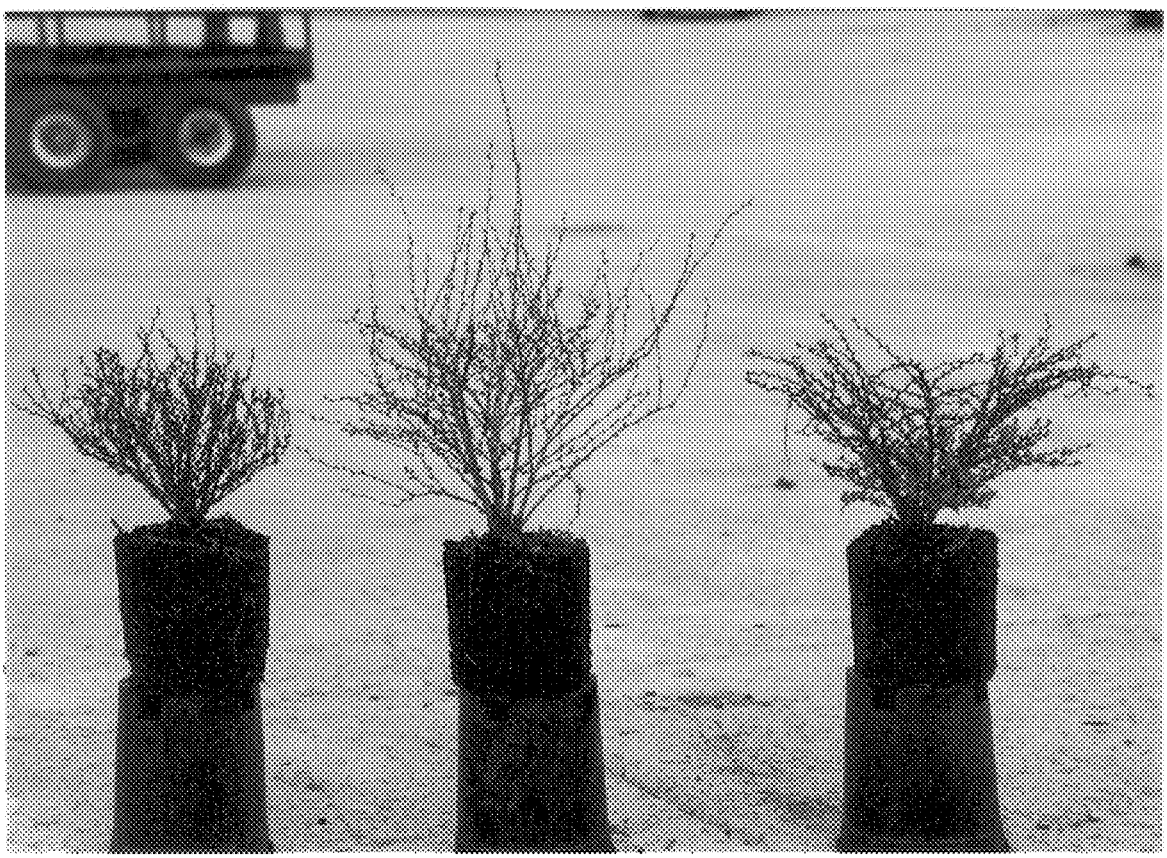
FIG. 3 depicts 3 year old container-grown plants and growth and branching habits. *Berberis thunbergii* 'Monlers', U.S. Plant Pat. No. 9,577 is on the left, an unnamed variety of *Berberis thunbergii* in the center and the new variety on the right. The differences in the branching habits are apparent with the upright vase shaped yet dwarf habit of the new variety. Note also the newly emerged foliage which presents itself earlier in the season when compared to the other selections.

Below is a detailed description of my new selection of *Berberis thunbergii* 'Monry', the color terminology is from The Royal Horticultural Society Colour Chart. Plant description taken from containerized plants February 1998 grown in Azusa, Calif. (unless otherwise noted.)

Overall size and habit: Deciduous, upright vase-shaped shrub. After ten years of age the plant has achieved a height of 1 meter and spread of 1 meter.

Flowers: Perfect; Full anthesis first week of February, early in comparison to cultivar Monlers and cultivar Aurea.

*Color.*—Petals: Six; Fully expanded Green — Yellow Group 1B and 1C Sepals: Six, Surrounding petals in bud stage prior to anthesis Orange — Red Group 32A. At anthesis Orange-Red Group 32A fades to Orange-Red Group 32D or fades to Green-Yellow Group 1B and 1C.

*Number.*—In fascicles of normally 4 though ranging from 2 to 5.

*Stems.*—Current growth exposed to sun — Yellow Group 3B. Current growth exposed to shade — Yellow-Green Group 145A. Mature — Greyed-Green Group 197C.

Foliage: appearing first week of February; early as cv. Monlers is in completely dormant state and Aurea just beginning to break dormancy.

*Arrangement.*—Alternate.

*Size.*—Lower shaded leaves 2.0 cm to 1.3 cm long; 8 mm to 6 mm wide Upper sun exposed leaves 1.5 cm to 1 cm long; 4 mm to 6 mm wide.

*Shape*.—Spatulate to broadly spathulate.

*Surface*.—Glabrous on upper and lower surface. Margins: entire, spine-tipped at apex (aristate), base narrowing into petiole (attenuate).

*Color*.—New growth in February first week. Tips: Orange-Red Group 30C. Upper Leaf Surface: Yellow-Green Group 144A. Lower Leaf Area: Green Group 143C. Mature growth: In July. Upper Leaf Surface: Green-Yellow group 1B mixed with Yellow-Green 144B. Lower Leaf Surface: Yellow Green Group 144C.

*Spines*.—Sometimes 3 parted central spine 5 mM–9 mm; usually 1 prominent spine 3 mm–7 mm long.

*Fruit*.—Red in Autumn, similar in size and color to other *Berberis thumbergii*.

Disease resistance: This new selection has been approved as black stem rust resistant.

I claim:

1. A new and distinct variety of Berberis plant as substantially shown and described herein that is characterized particularly as a novelty by the unique combination of early flower clusters and yellowish foliage produced along terminal branch tips and an upright vase-shaped shrub habit with brilliant yellow mature foliage that tolerates full sun without burning.

* * * * *